US00PP12861P2

(12) United States Plant Patent
Loison

(10) Patent No.: US PP12,861 P2
(45) Date of Patent: Aug. 20, 2002

(54) PINEAPPLE PLANT NAMED 'RL 41'

(75) Inventor: Chantal Loison, Montpellier (FR)

(73) Assignee: Cirad, Montpellier (FR)

( * ) Notice: Subject to any disclaimer, the term of this patent is extended or adjusted under 35 U.S.C. 154(b) by 0 days.

(21) Appl. No.: 09/603,903

(22) Filed: Jun. 26, 2000

(30) Foreign Application Priority Data

Jul. 15, 1999 (FR) ..... 016823

(51) Int. Cl.[7] ..... A01H 5/00
(52) U.S. Cl. ..... Plt./156
(58) Field of Search ..... Plt./156

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

An *Ananas comosus* variety is provided that forms attractive orange-red oval to cylindrical fruit with relatively flat fruitlets. The fruit is substantially uniformly colored from top to bottom when ripe even in the absence of chemical treatment with a growth regulator. The fruit flesh is golden yellow and substantially homogeneous. When compared to Smooth Cayenne (non-patented in the United States), the fruit flesh in generally sweeter and commonly contains substantially more ascorbic acid. Such higher ascorbic acid content is of nutritional benefit and serves to retard the browning of the flesh. Completely spineless piping leaves are formed. On an infrequent basis peduncle slips are formed that commonly are spaced below the fruit and do not to pose any significant interference. The fruit crown is long, erect, and conical. The fruit yield is generally comparable to that of Smooth Cayenne.

2 Drawing Sheets

SUMMARY OF THE INVENTION

Figure 1:
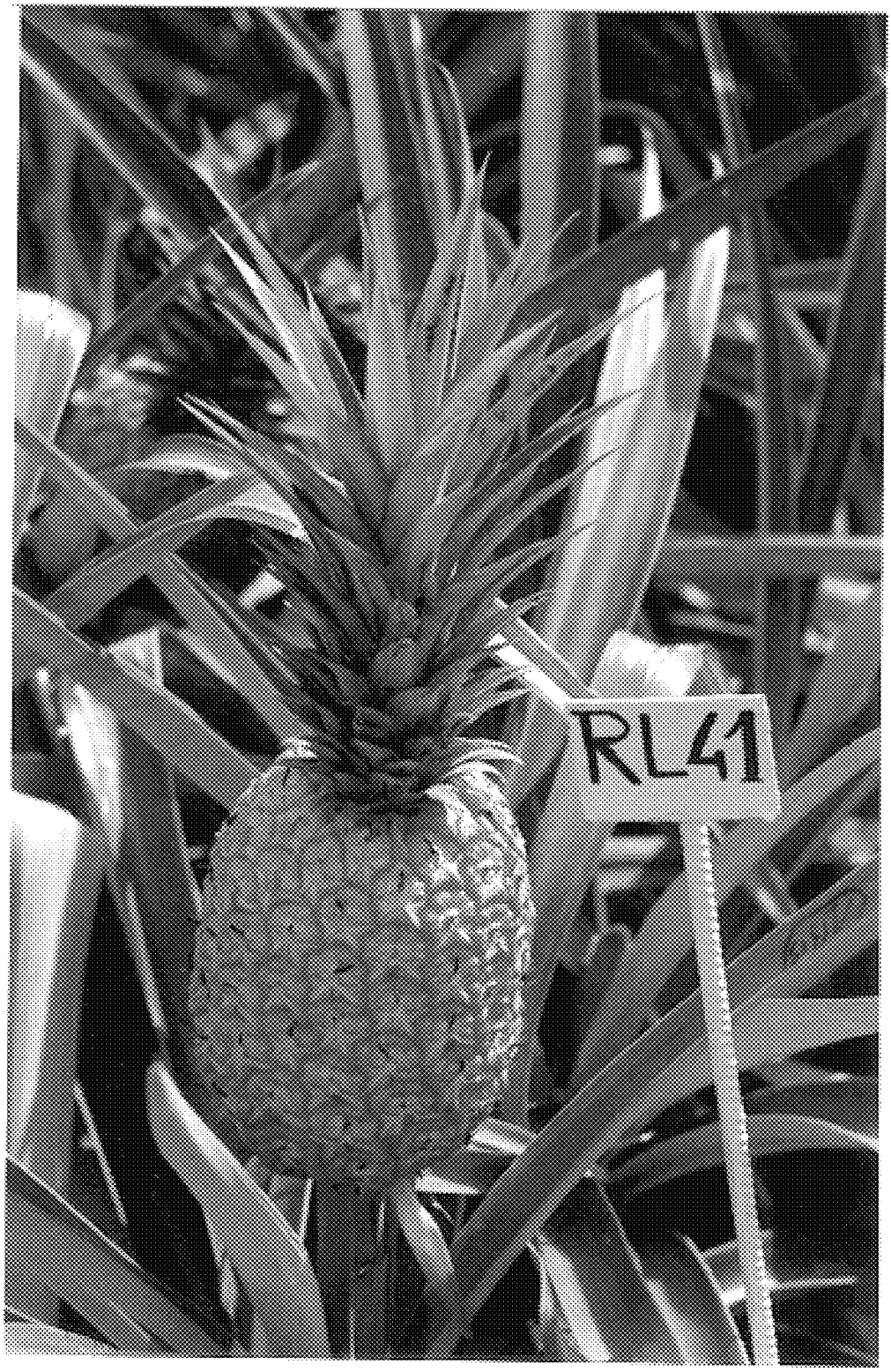

The new variety *Ananas comosus* was created in 1988 at Martinique (French West Indies) by artificial pollination wherein two parents were crossed which previously had been studied in the hope that they would contribute the desired characteristics. The female parent (i.e., the seed parent) of the new variety was the Smooth Cayenne 'HA 10' variety (non-patented in the United States). This female parent was a typical "Hawaiian Type" pineapple. The male parent (i.e., pollen parent) was the Manzana 'CO 24' variety (non-patented in the United States). The male parent is grown primarily in Columbia at high altitudes for local consumption and commonly is not exported. The parentage of the new variety can be summarized as follows:

Smooth Cayenne 'HA 10'×Manzana 'CO 24'.

Objectives of the breeding program included the creation of a new Pineapple variety which displays a more cylindrical fruit configuration, greater resistance to the browning of the fruit flesh, a more attractive fruit shell appearance, and completely spineless leaves.

The seeds resulting from the above pollination were sown and approximately 200 small plants were obtained which were different from each other. The first fruit was harvested in 1990. Selective study during 1990 to 1998 resulted in the identification of a single plant of the new variety.

It was found that the new Pineapple variety of the present invention possesses the following combination of characteristics:

(a) Forms attractive orange-red oval to cylindrical fruit that is substantially uniformly colored from top to bottom when ripe with relatively flat fruitlets, (b) Forms substantially homogeneous golden yellow fruit flesh that generally is sweeter than that of Smooth Cayenne and commonly contains substantially more ascorbic acid than that of Smooth Cayenne, (c) Forms completely spineless piping leaves, (d) Infrequently forms peduncle slips that originate at a spaced location below the fruit, (e) Forms a long conical crown, and (f) Commonly produces fruit in substantially the same yield as Smooth Cayenne.

The new variety of the present invention readily can be distinguished from each of the parent varieties.

When compared to Smooth Cayenne 'HA 10', the new variety exhibits spineless piping leaves wherein the lower epidermis and mesophyll are folded over the upper leaf surface. On the contrary the leaves of a Smooth Cayenne are smooth only on the lower and middle portions and are spiny elsewhere. The fruit shape, crown shape, and fruit shell color are different. The internal fruit flesh possesses greater homogeneity when ripe, generally a greater sweetness, and substantially more ascorbic acid that minimizes a tendency to darken when exposed. The presence of peduncle slips is extremely rare in Smooth Cayenne. The fruit flesh also emits a different aroma as evidenced by chromatographic analysis. Chemical treatment with a growth regulator (e.g., with 2-chloroethylphosphonic acid) to create more uniform fruit shell coloration is not necessary with the new variety. Also, the fruit of the new variety commonly is ready for harvest in a lesser period of time following forcing. The overall fruit yield of the new variety is approximately the same as that of Smooth Cayenne. In some tests the yield has ranged from 85 to 105 percent that of Smooth Cayenne.

When compared to the Manzana 'CO 24', the new variety exhibits a different fruit shape, a significantly lesser frequency of multiple crowns, a geater sugar content, a lesser ascorbic acid content, better fruit flesh homogenity when ripe, a smaller core diameter, and improved sucker production. The fruit flesh also emits a different aroma as evidenced by chromatographic analysis.

The cultivation requirements of the new variety including density, fertilization, and disease and pest control are believed to be substantially the same as those commonly employed with Smooth Cayenne. A typical plant of the new variety commonly measures approximately 90 cm in height and approximately 120 cm in width at the broadest point. Climatic and cultural conditions will influence the plant size.

The new variety has been found to undergo asexual propagation in Martinique (French West Indies) by the use of suckers as well as in vitro propagation. The first sucker is harvested slightly later than for Smooth Cayenne; however, the total number of suckers available for harvest is greater. Asexual propagation by these routes as performed in Martinique has shown that the characteristics of the new variety are strictly transmissible from one generation to another.

The new variety has been named 'RL 41'.

BRIEF DESCRIPTION OF THE PHOTOGRAPHS

The accompanying photographs show as nearly true as it is reasonably possible to make the same in color illustrations of this character, a plant specimen and fruit of the new variety. The plants were reproduced from suckers and were being grown at Martinique during October, 1999. The age of the plants was approximately 14 months.

FIG. 1—illustrates a typical specimen of the plant and fruit of the new variety. The spineless piping leaves are included.

Figure 2:
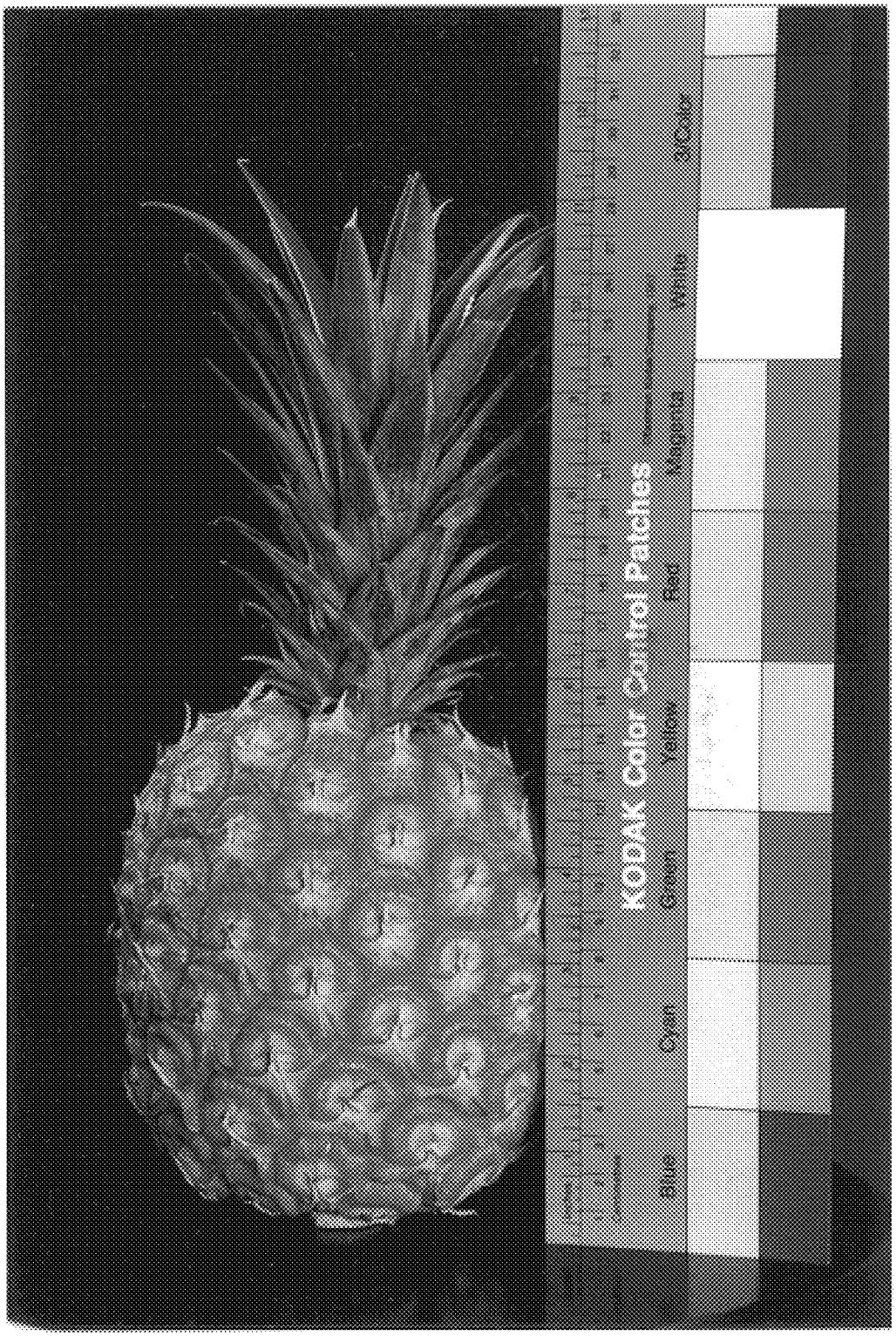

FIG. 2—illustrates a close up side view of a typical near ripe fruit of the new variety. The attractive uniform orange-red appearance of the oval to conical fruit is shown as well as a single long erect conical crown. At the right is a measuring stick in inches and centimeters. Standard KODAK Color Control Patches also are included for comparative purposes.

DETAILED DESCRIPTION

The chart used in the identification of colors is that of The Royal Horticultural Society (R.H.S. Colour Chart), London. In some instances terminology is utilized to indicate the corresponding colors in more common terms. Such terminology is to be accorded its ordinary dictionary significance. The description is based upon the observation of plants growing in Martinique that had been forced approximately 8 months following planting. The fruits were ready for harvest approximately 5 months following forcing. The harvest date will be greatly influenced by climatic conditions. The plants had been asexually reproduced from suckers.

Botanical classification: *Ananas comosus*, var. 'RL 41'.

Parentage:

*Seed parent*.—Smooth Cayenne 'HA 10'.

*Pollen parent*.—Manzana 'CO 24'.

Propagation: Holds its distinguishing characteristics well through asexual propagation by the use of suckers and the use of in vitro propagation.

Stems:

*General*.—Short, upright and sheathed with overlapping leaves, with each leaf axil having a dormant axillary bud.

*Texture*.—Glabrous and fleshy.

*Size*.—Commonly approximately 28 to 35 cm in length at anthesis.

*Shape*.—Terete and tapered somewhat to a narrower diameter at soil level.

Leaves:

*General*.—Closely overlapping sessile leaves (formed in acropetal succession) forming a dense rosette. Commonly number approximately 50 to 80 and have 5/13 phyllotaxy. Often approximately 40 leaves are emitted between planting and forcing.

*Texture*.—The upper epidermal area in glabrous, semi-rigid and channeled (or concave) except at the leaf tip. The lower epidermal area is finely striated in the longitudinal direction and appears to be covered with a white furfuraceous layer consisting of scale-like trichomes.

*Leaf arrangement*.—Alternate and rosulate.

*Leaf margins*.—Plain, and completely without spines as the lower epidermis and mesophyl are folded over the upper leaf surface. Accordingly, piping leaves are formed.

*Leaf venation*.—Substantially parallel.

*Leaf configuration*.—Leaves commonly are not uniform in shape and vary with the position of the leaf on the stem. The basal or oldest leaves are lanceolate in form while the base is considerably expanded. There is a decided narrowing in the width between non-chlorophyllous (basal) and chlorphyllous (or main body) portions of the leaves. The longest or most mature leaves are lanceolate in form and the base is without the arcuate expansions of the preceding leaves. The remaining leaves (or center leaves of the plant rosette) are lanceolate in form with no expansion of width into a distinct base.

*Leaf size*.—At anthesis the length commonly ranges from approximately 80 to 120 cm for those leaves originating from the central part of the stem, and the width commonly is approximately 6 to 7 cm at the central area of the longest leaves.

*Color* (*upper epidermal surface*).—In general the coloration is usually dominated by olive green tinged with greyed-purple. The edge of the leaf commonly has greyed-green (piping). The field of the basal disk area is dominated by white to green coloration. More specifically, the achlorophyllous basal disk area is white to green, White Group 155D to Green-White Group 157D. The mid-leaf area commonly is olive green, Green Group 137A to 137B, on the margins, and tinged with greyed-purple in the center, Greyed-Purple Group 187 A to187C. The edges are Greyed-Green Group 194A to 194B. The leaf tip area commonly is of the same coloration as the mid-leaf area.

*Color* (*lower epidermal area*).—In general the coloration commonly is greyish olive-green, Greyed-Green Group 194A to 194B, and is disclored at the basal area. More specifically, the basal disk area commonly ranges from White Group 155D to Green-White Group 157D.

Inflorescence:

*General*.—A composite flower with approximately 80 to 120 fruitlets per inflorescence is borne on a long peduncle having a length of approximately 27 cm at the apical meristem. Individual bi-sexual flowers consist of three sepals, six stamens, three stigmas, and three carpels. The inflorescence is self-incompatible producing edible fruit parthenocarpically.

*Texture*.—Glabrous and fleshy.

*Shape*.—Oval with slightly raised flowers with a green crown. Crown leaves are short and erect at anthesis.

*Size and color*.—The flowering proceeds from bottom to top to yield an inflorescence that displays a coloration of Violet-Blue Group 89A. The peduncle is a deep pink, Red Group 46C. The petal length is medium and commonly ranges from approximately 18 to 22 mm. The stamen length commonly is up to 15 mm. The style length commonly is up to 17 mm. The sepal length commonly is approximately 7 to 9 mm. The pollen quantity is sparse.

Fruit:

*Size.*—Commonly approximately 1 to 2 Kg in weight with a crown of approximately 150 to 300 g. The size of the fruit is directly influenced by the size of the plant at the flowering stage. Sometimes a multiple crown is observed but these tend to be erect and accordingly are less detrimental to the overall fruit appearance.

*Shape.*—Cylindrical to oval with large relatively flat fruitlets. The crown is long, conical, and erect.

*Core diameter.*—Under the same growing conditions 26 mm for the new variety of the present invention, 32 mm for 'HA 10', and 38 mm for 'CO 24'.

*Bearing.*—From the apical meristem of the plant on a long peduncle that commonly measures approximately 24 to 30 cm in length.

*Shell color.*—With advancing maturity the color changes dark green-brown to green to orange and to orange-red approaching red. With maturity the coloration commonly passes through Orange Group 25A, Orange Group 28A, Orange-Red Group 32A, Orange-Red Group 33A, Orange-Red Group 33B, and then to near Red Group 42A and 42B at full maturity. The color of the shell from top to bottom is more uniform than in Smooth Cayenne.

*Edible flesh.*—Before maturity the flesh is white to green white, White Group 155D to Green-White Group 157D. At maturity the flesh commonly is golden yellow, Yellow Group 13B to 13C, to yellow-orange, Yellow-Orange Group 14C. The color of the mature flesh from top to bottom is more uniform than in Smooth Cayenne.

*Brix level.*—Typically ranges from approximately 14 to 20 degrees, or more. Is influenced somewhat by climatic conditions, mineral nutrition, and the size and maturity of the fruit. In a comparative test under the same growing conditions a Brix of 12 was observed for 'CO 24', a Brix of 16 for 'HA 10', and a Brix of 17 for the new variety of the present invention. The difference in Brix level from top to bottom of the fruit typically is less than in Smooth Cayenne. For example, during a test such Brix difference was 1.5 in the variety of the present invention, and 2.2 in Smooth Cayenne.

*Ascorbic acid level.*—Commonly 5 to 30 mg/100 ml, is more than Smooth Cayenne, and is less than Manzana. Is often twice the level of Smooth Cayenne. In Smooth Cayenne the ascorbic acid level commonly is 2 to 12 mg/100 ml, and in Manzana 40 to 120 mg/100 ml. Higher ascorbic acid levels are desirable from a nutritional standpoint and also slow down to aging and darkening of the fruit flesh.

*Total acid level.*—Commonly 9 to 12 m.e.q./100 ml. The acidity of the Smooth Cayenne typically is lower than that of the new variety of the present invention.

*Citric acid level.*—Typically is approximately 0.72 g/100 g. This can be compared to a value of approximately 0.63 g/100 g for the Smooth Cayenne.

*Malic acid level.*—Typically is approximately 0.21 g/100 g. This can be compared to a typical value of approximately 0.12 g/100 g for the Smooth Cayenne.

*Flesh carotenoids* (*all trans B carotene*).—Typically 214 μg/100 g. This can be compared to a typical value of 80 μg/100 g for the Smooth Cayenne.

*Shell carotenoids* (*all trans B carotenoids*).—Typically 665 μg/100 g. This can be compared to a typical value of 586 μg/100 g for the Smooth Cayenne.

*Shell anthocyanins* (*all cyanide 3 glucoside*).—Typically 544 μg/100 g. This can be compared to a typical value of 359 μg/100 g for the Smooth Cayenne.

*Disease resistance.*—Generally comparable to Smooth Cayenne when grown under the standard growing conditions of Martinique.

I claim:

1. A new and distinct variety of *Ananas comosus* plant having the following combination of characteristics:

(a) Forms attractive orange-red oval to cylindrical fruit that is substantially uniformly colored from top to bottom when ripe with relatively flat fruitlets, (b) Forms substantially homogeneous golden yellow fruit flesh that generally is sweeter than that of Smooth Cayenne and commonly contains substantially more ascorbic acid than that of Smooth Cayenne, (c) Forms completely spineless leaves, (d) Infrequently forms peduncle slips that originate at a spaced location below the fruit, (e) Forms long a conical crown, and (f) Commonly produces fruit in substantially the same yield as Smooth Cayenne;

substantially as herein shown and described.

* * * * *